(12) United States Patent
Varady et al.

(10) Patent No.: US 9,717,546 B2
(45) Date of Patent: Aug. 1, 2017

(54) CRYOTHERAPY DEVICE AND METHOD FOR THE TREATMENT OF CERVICAL PRECANCEROUS LESIONS

(71) Applicants: Marton Varady, Baltimore, MD (US); Shuja T. Dawood, Santa Clara, CA (US); John-William Sidhom, Westfield, NJ (US); Enriquito Lu, Baltimore, MD (US)

(72) Inventors: Marton Varady, Baltimore, MD (US); Shuja T. Dawood, Santa Clara, CA (US); John-William Sidhom, Westfield, NJ (US); Enriquito Lu, Baltimore, MD (US)

(73) Assignee: Jhpiego Corporation, Baltimore, MD (US)

( * ) Notice: Subject to any disclaimer, the term of this patent is extended or adjusted under 35 U.S.C. 154(b) by 1108 days.

(21) Appl. No.: 13/898,962

(22) Filed: May 21, 2013

(65) Prior Publication Data

US 2014/0350535 A1    Nov. 27, 2014

Related U.S. Application Data

(60) Provisional application No. 61/649,550, filed on May 21, 2012.

(51) Int. Cl.
  *A61B 18/02* (2006.01)
  *A61B 18/00* (2006.01)

(52) U.S. Cl.
  CPC .......... *A61B 18/0218* (2013.01); *A61B 18/02* (2013.01); *A61B 2018/00005* (2013.01); *A61B 2018/00011* (2013.01); *A61B 2018/00017* (2013.01); *A61B 2018/00023* (2013.01); *A61B 2018/00035* (2013.01); *A61B 2018/00559* (2013.01); *A61B 2018/00577* (2013.01); *A61B 2018/00583* (2013.01); *A61B 2018/025* (2013.01); *A61B 2018/0212* (2013.01); *A61B 2018/0225* (2013.01); *A61B 2018/0231* (2013.01); *A61B 2018/0237* (2013.01); *A61B 2018/0243* (2013.01); *A61B 2018/0256* (2013.01); *A61B 2018/0262* (2013.01);
(Continued)

(58) Field of Classification Search
  USPC .......................................... 606/21
  See application file for complete search history.

(56) References Cited

U.S. PATENT DOCUMENTS 6,000,238 A * 12/1999 Hollingshead .......... A23L 3/375
                                                    62/603
6,141,985 A    11/2000 Cluzeau
(Continued)

*Primary Examiner* — Joseph Stoklosa
*Assistant Examiner* — Jennifer Le
(74) *Attorney, Agent, or Firm* — Larry J. Guffey

(57) ABSTRACT

A device for providing a cryotherapy ablation treatment includes a piping assembly and a snow horn adapted to create a spray of snow from a pressurized source of a low-temperature liquid, a tubular applicator for collecting a mass of snow at a prescribed density that is sufficient to allow the mass to serve as the needed, low temperature, thermal reservoir for the device after the applicator's distal end has been disconnected from the snow horn end so that it can to be used during the treatment process, and an applicator tip adapted to allow it to connect to the applicator's distal end and be used to treat those specific locations which are to receive this treatment.

8 Claims, 3 Drawing Sheets

(52) U.S. Cl.
CPC ............... *A61B 2018/0275* (2013.01); *A61B 2018/0287* (2013.01); *A61B 2018/0293* (2013.01)

(56) References Cited

U.S. PATENT DOCUMENTS

| | | | |
|---|---|---|---|
| 6,629,417 B2 | 10/2003 | Haas | |
| 6,960,202 B2 | 11/2005 | Cluzeau | |
| 2006/0213509 A1 | 9/2006 | Marin | |
| 2008/0119839 A1* | 5/2008 | Vancelette | A61B 18/02 606/23 |
| 2011/0060323 A1* | 3/2011 | Baust | A61B 18/02 606/21 |
| 2013/0079761 A1 | 3/2013 | Baust | |

* cited by examiner

CRYOTHERAPY DEVICE AND METHOD FOR THE TREATMENT OF CERVICAL PRECANCEROUS LESIONS

CROSS-REFERENCE TO RELATED APPLICATION

This application claims the priority and benefits of U.S. Provisional Patent Application No. 61/649,550, filed May 21, 2012 by the present inventors and entitled "CRYOTHERAPY DEVICE AND METHOD FOR THE TREATMENT OF CERVICAL CANCER." The teachings of this application are incorporated herein by reference to the extent that they do not conflict with the teaching herein.

BACKGROUND OF THE INVENTION

1. Field of the Invention

The present invention relates generally to surgery devices and methods. More particularly, the present invention relates to a cryotherapy device and method to treat, destroy or ablate a patient's abnormal tissues or lesions, e.g., for the ablation of cervical, precancerous lesions to prevent cervical cancer.

2. Description of the Related Art

Cervical cancer is the third most common cancer in the world. Moreover, eighty percent of all cervical cancer cases occur in the developing world. With approximately 500,000 new cases each year, cervical cancer is responsible for over 250,000 deaths per year, making it the second leading cause of death in developing countries. Many of these deaths are women in their late 30s and early 40s, thus compromising the health and well-being of the surrounding family. Indeed, this is especially true for the children of these women, who often fall behind in their education and may be abandoned, without a mother.

While steps, such as annual PAP smears and other interventional methods, have been taken to eradicate cervical cancer in the developing world, cervical cancer still remains a large burden for these countries. Its prevalence in the developing world can in large part be attributed to a lack of appropriated technologies for screening and treatment.

A "single visit" approach has been developed and includes a screening by visual inspection with acetic acid and a point-of-diagnosis cryotherapy treatment. This approach for screening and treatment has provided a safe, acceptable, and feasible option in low-resource settings.

Cryotherapy includes freezing the abnormal cervical tissue with a coolant such as carbon dioxide, $CO_2$, and has been used for over forty years to treat cervical dysplasia. This process uses what is called a "double freeze procedure." One freezes the cervix for three minutes and then allows it to thaw for five minutes, then it is frozen again for an additional three minutes. This procedure maximizes the amount of tissue that is frozen more so than just doing one extra-long freeze because the frozen tissue becomes more thermally conductive after the first freeze so the second freeze penetrates quicker and subsequently deeper into the affected tissue.

Cryotherapy is the leading method for the ablation of cervical precancerous lesions for the prevention of cervical cancer, especially in the developing world. Despite proven efficacy of cryotherapy as a mode of ablating precancerous lesions, the current state of the art used to facilitate cryotherapy is not sufficiently designed for widespread and reliable use in the developing world.

While this single visit approach or "screen and treat" program has been shown to be effective in prevention of cervical cancer, there still remains a hurdle to scaling up such a program for widespread impact. While cryotherapy using $CO_2$ has been shown to be safe and effective, even in the hands of low-level health care workers, the equipment is not necessarily suitable to be widely dispersed. Indeed, cryotherapy tools can be expensive, technically complex, lacking portability, and difficult to repair in the field.

Currently, the developing world utilizes cryoguns, see, for example, U.S. Pat. No. 4,377,168 which discloses expanding pressurized $CO_2$ (or $N_2O$ in some instances when a country or program can afford the added expense of the $N_2O$) against a thermally conductive tip. The expansion of the $N_2O$ in this closed system creates a temperature of approximately −50 to −70 degrees C. on the surface of the tip which is in contact with a lesion.

With carbonated beverage manufacturers being widely dispersed in the developing world, and often using carbon dioxide to produce their carbonated beverages, carbon dioxide manufacturers are also widely dispersed in the developing world. This has led to cryoablation being conducted with carbon dioxide as the primary source of coolant.

The current design of cryotherapy tools suffers from several flaws when utilized with carbon dioxide tanks, including: water vapor leaving the tank causes tip blockages, non-medical grade carbon dioxide may have particulates, which cause tip blockages, and a pressure drop may occur in the cylinder through the cooling process during extended use which results in warmer and less effective tip temperatures.

Additionally, the equipment was never originally designed for use within the extreme conditions of the developing world where there are high volumes of ablations along with environmental abuse of the product. First, the tips on the current cryotherapy tools are manufactured with gold or chrome plating, which not only makes the tip expensive, at approximately three hundred dollars per tip, but these tips also suffer from corrosion from the chlorine disinfection method—the widely available method for sterilization in the developing world.

Improper cleaning and storage of these tips also leads to clogs, requiring replacement. Additionally, the overall cost of the equipment is around thirteen hundred to two thousand dollars per device. Moreover, with the complexity of this equipment's engineering design, there is a lack of repair knowledge and backup parts when the equipment breaks down. Unfortunately, when the cryotherapy equipment malfunctions in the field, the device becomes unused and is rarely capable of being easily fixed.

Finally, the amount of carbon dioxide required per treatment limits the portability of the device. A tank containing 50 lbs of $CO_2$, weighs approximately 160 lbs total, and treats only about 10 to 15 patients. These large tanks are therefore difficult to transport to the rural areas where women need to be screened and treated, either in the context of health centers, mobile health vehicles or organized screen & treat camps. Therefore, these characteristics of current cryotherapy equipment prohibit its massive scale-up for widespread impact on reducing the burden of cervical cancer.

It would therefore be advantageous to provide a device and method that could safely, effectively, and in a low-cost manner treat, destroy or ablate cervical, precancerous lesions in order to prevent cervical cancer.

SUMMARY OF THE INVENTION

Recognizing the need in emerging nations for the development of improved cryotherapy techniques, the present invention is generally directed to satisfying this need. The present invention's method of treatment or process for providing cryotherapy ablation utilizes a pressurized tank of a low-temperature liquid as its source for the low-temperature, thermal reservoir that is needed to conduct by this process.

A preferred embodiment of the present invention takes the form of a device that includes: (a) a piping assembly having a configuration adapted to allow the assembly's distal end to connect to the pressurized tank's outlet and thereby allow the low-temperature liquid to exhaust through the assembly in such a manner that yields the proper liquid flow conditions at the assembly's proximal end so as to create a spray of snow as a result of the freezing of the low-temperature liquid as it exhausts from the piping assembly, (b) a tubular, snow horn having a boundary wall that extends between distal and proximal ends and has a configuration adapted to allow the snow horn's distal end to connect to the piping assembly's proximal end so as to cause the exhausting low-temperature liquid to flow through the snow horn and create the flow conditions in the snow horn that will enable a prescribed mass of this snow of a desired density to be collected in a specified period of time, (c) a tubular applicator having a configuration adapted to allow the applicator's distal end to temporarily connect to the snow horn's proximal end in order to enable the prescribed mass of this snow to be collected and wherein this mass of collected snow is sufficient to allow it to serve as the needed, low temperature, thermal reservoir for the device after the applicator's distal end has been disconnected from the snow horn end so that the applicator can be used during the cryotherapy ablation process, and (d) an applicator tip having a configuration adapted to allow the applicator tip to connect to the applicator's distal end and used during a cryotherapy ablation process to locate on a patient those specific locations which are to receive this treatment.

A first variant of this preferred embodiment further includes a hand-operable handle having a configuration adapted to allow it to control the positioning of the applicator's distal end during a cryotherapy ablation treatment.

A second variant of this preferred embodiment further includes a push rod having a configuration adapted to allow the push rod's distal end to variably extend into the applicator so as to allow a base attached to the push rod's distal end to serve as the furthest point in the applicator, as measured from its distal end, that the spray of snow can collect.

A third variant of this preferred embodiment further includes a means for biasing the push rod so that its base pushes the mass of collected snow towards and against the applicator tip during a cryotherapy ablation process.

A fourth variant of this preferred embodiment further includes adapting the configuration of the push rod so that it can interact with the handle to control the location of the push rod's base relative to the applicator's distal end.

A fifth variant of this preferred embodiment includes further configuring all of the elements of the device so that optimally suited for use in a cryotherapy ablation process which utilizes the low-temperature liquid of carbon dioxide.

A sixth variant of this preferred embodiment includes further configuring all of the elements of the device so that optimally suited for use in a cryotherapy ablation process associated with the removal of cervical, precancerous lesions for the prevention of cervical cancer.

Another preferred embodiment of the present invention takes the form of a method for providing a patient with cryotherapy ablation and the steps of this method include utilizing the device as recited in any one of its variations that are summarized above.

Thus, there has been summarized above (rather broadly and understanding that there are other preferred embodiments which have not been summarized above) the present invention in order that the detailed description that follows may be better understood and appreciated.

DESCRIPTION OF THE PREFERRED EMBODIMENT

Figure 1A:
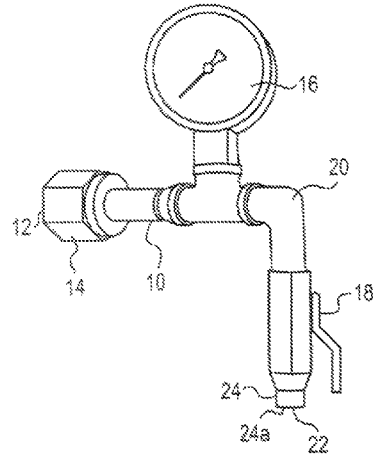
FIG. 1(a) is a perspective view of the piping assembly of the present invention.

Before explaining at least one embodiment of the present invention in detail, it is to be understood that the invention is not limited in its application to the details of construction and to the arrangements of the components or elements set forth in the following description or illustrated in the drawings. This invention is capable of being practiced and carried out in various ways. Therefore, it is to be understood that the present invention is not to be limited to the specific embodiment disclosed herein, and that its many variants are intended to be included within the scope of the appended claims. Also, it is to be understood that the phraseology and terminology employed herein are for the purpose of description and should not be regarded as limiting. In the accompanying drawings, like numbers refer to like elements throughout.

"A preferred embodiment in accordance with the present invention 1 provides an apparatus or device and method that utilizes cryotherapy to treat, destroy or ablate a patient's abnormal tissues or lesions, e.g., for the ablation of cervical, precancerous lesions for the prevention of cervical cancer. The device includes an auxiliary piping assembly 10 that is configured to be connected to the typically horizontally-directed outlet of a pressurized, carbon dioxide tank in the bottom of which resides liquid carbon dioxide, CO2, or other suitable fluid that freezes at a comparatively low temperature (i.e., a low-temperature liquid)."

The purpose of this piping assembly and its configuration is adapted to yield the proper flow conditions for the beginning of the creation of the $CO_2$ snow from the distal end of the piping assembly when the pressurized tank of carbon dioxide is allowed to exhaust through the piping assembly at operating pressures in the range of 750-850 psig and the $CO_2$ freezes as it exits the assembly. See U.S. Pat. No. 6,543,251 and European Patent Number (EP) 1,046, 614B1 for background technology related to the creation of $CO_2$ snow, One variant for the configuration of this piping assembly 10 includes a distal end 12 that has an adapter 14 which allows the piping assembly to be connected and firmly affixed to the tank's outlet 2, while also reducing the diameter of the pipe through which the exhaust is flowing. See FIG. 1(a).

A pressure gauge 16 that is sized to measure and read pressures up to approximately 700-1,000 psig is included in this piping assembly so as to check to ensure that the tank pressure is adequate to support the creation of $CO_2$ snow. It also includes a valve 18 that regulates flow through the piping assembly, a ninety degree elbow 20 that is used to redirect the normal direction of the flow from the tank from being horizontal to vertical, and a proximal end 22 to which is attached a nozzle 24 whose outlet or orifice 24a diameter is critical to the efficient operation of the piping assembly and it's on-demand, capability to begin the creation of $CO_2$ snow.

Figure 1B:
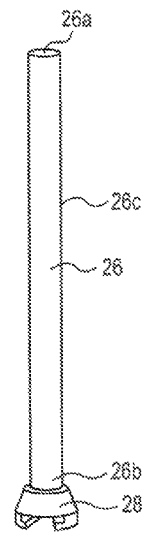
FIG. 1(b) is a perspective view of the snow horn of the present invention.

A preferred variant of this piping assembly's distal end has the diameter of the pipe to which the nozzle connects being ⅛ of an inch and the diameter of the nozzle's orifice 24a being in the range of 0.005-0.050 inches, with a preferred value of 0.016 inches. Downstream from this nozzle and its orifice 24a is a snow horn 26 which has a boundary wall 26c and a configuration adapted to create the final flow conditions for the collection of $CO_2$ snow having a desired density. Alternatively, the snow horn has a configuration adapted to create the proper flow conditions at the snow horn's proximal end so as to enable a prescribed mass of the snow of a desired density to be collected in a specified period of time. See FIG. 1(b). This snow horn has a distal end 26a that has a configuration that allows it to be locked to a comparable fitting (e.g., ⅛ inch NPT tap) on the proximal end 22 of the piping assembly. The proximal end 26b of this snow horn has a special fitting or coupling 28 that allows for it to be easily connected to and disconnected from the distal end 34 of the device's applicator 30. This coupling 28 is also configured as the element of the device which has the least structural strength. The purpose of this is to ensure that the device will break apart at this coupling during a situation in which an accident were to occur and an excess $CO_2$ pressure were to be applied to the device.

The $CO_2$ snow's desired density is chosen so that the mass of $CO_2$ snow collected is sufficient to provide the needed low temperature reservoir while also allowing the scale of the device to be such that it is appropriate for the desired cryotherapy procedure. Experimentation has shown that a $CO_2$ snow density in the range of 8-11 $g/in^3$ allows the required mass of snow to be in the range of 8-10 g for a normal preventive, ablation of cervical, precancerous lesions procedure.

The present invention also includes a hollow, tubular applicator 30 which has proximal 32 and distal 34 ends. As its name implies, this part of the present invention is used by a health care provider to help precisely locate the point/s on a patient where the invention's cryotherapy will be applied. This applicator 30 has a configuration that is adapted to collect and temporarily store in its interior 36 and proximate its distal end the mass 6 of $CO_2$ snow that is required (i.e., sufficient to allow the mass of collected snow to serve as the low temperature thermal reservoir for the device after the applicator's distal end has been disconnected from the snow horn and the applicator's tip attached so the applicator and its tip together can be used to perform a cryotherapy ablation).

Figure 1C:
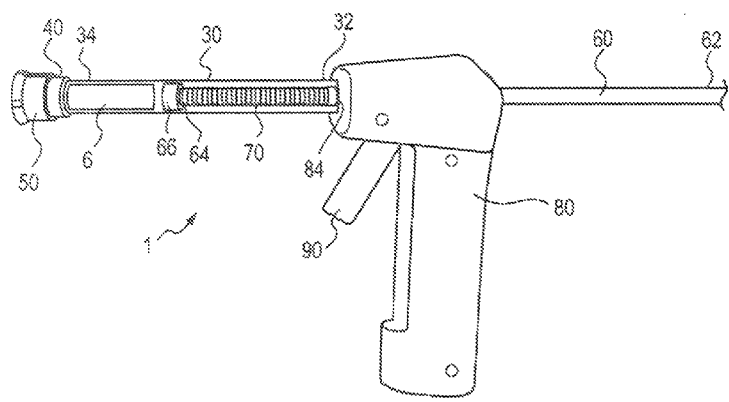
FIG. 1(c) is a perspective view of the, assembled and filled with $CO_2$ snow, applicator, applicator tip, push rod, spring and handle of the present invention.
Figure 2:
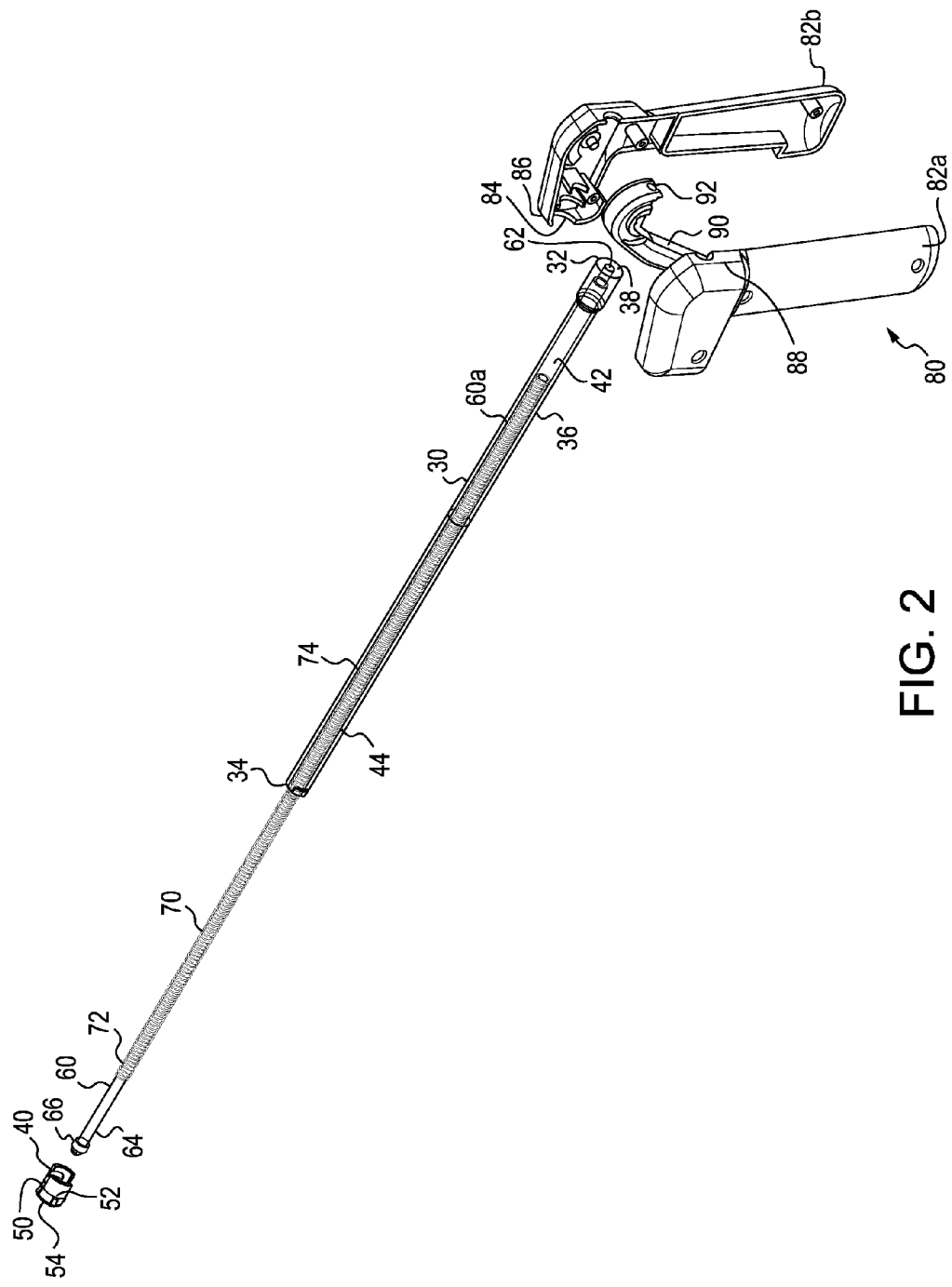
FIG. 2 is an exploded, perspective view of the elements of the present invention shown in FIG. 1(c).

See FIG. 1(c). See also FIG. 2 which is an exploded, perspective view of the elements of the present invention that are shown in FIG. 1(c).

A flow-through fitting 40 is provided at the applicator's distal end that is configured to allow for, among other things, the attachment and detachment of the applicator's distal end to and from the coupling 28 on the distal end of the snow horn during the part of the process in which the applicator is filled with $CO_2$ snow. This same fitting 40, upon being decoupled from the snow horn, is also configured to allow it to be used for attaching to the applicator's distal end an especially designed applicator cap or tip 50 which is the part of the device that actually comes into contact with a patient's body where it is desired to freeze and ablate targeted tissues or cells.

The proximal end 32 of the applicator has an opening 38 that allows access to the applicator's interior from this proximal end. This opening allows for a base 66 at the distal 64 end of a retractable, push rod 60 to be inserted to different distances into the applicator. The outer boundaries of this base have a configuration that is adapted to allow them to provide a sliding seal against the applicator's interior wall 42. The distal portion of this base, when the push rod is adjustably inserted into the applicator, thus forms the furthest boundary at which $CO_2$ snow may accumulate in the applicator. The wall 42 of the applicator is also provided with a number of vent holes 44 by which gases can be vented during the $CO_2$ snow filling process.

In the alternate venting pattern, channels running parallel to the axis of the cylinder allow gas venting to the atmosphere at both the proximal 32 and distal 34 ends of the applicator. The opening to each of the channels is sufficiently small such that the particles of snow do not coagulate in this region in such a way as to block the channels. The channels may also serve to vent the sublimating gas during a cryotherapy treatment procedure and thereby prevent accumulation of the sublimate in the vaginal cavity which inhibits the device operator's ability to see the distal end of the applicator.

The exact dimensions of such an applicator will obviously be a function of the type of cryotherapy procedure that is desired to be performed using the present invention. For a normal preventive, ablation of cervical, precancerous lesions procedure, typical dimensions for this applicator are: outer diameter=⅝ inch, wall thickness=1/16 inch when polycarbonate extruded tubing is being used as the material from which to fabricate the tube, length in the range of 6-8 inches, vent holes: diameters in the range of 0.02-0.03 inches and 15-20 in number and spaced at 0.25 inch intervals along the length of the tube. For an applicator sized in this manner, typical snow horn dimensions would then be: length=7-9 inches, inside tube diameter=⅜ inch and where it may be fabricated from an assortment of plastics, including polycarbonate, acrylic, polysulfone, ABS, acetal copolymer, or polypropelene.

Once the applicator is sufficiently filled with $CO_2$ snow, the applicator is disconnected from the snow horn and an applicator cap or tip 50 is attached to the fitting 40 on the applicator's distal end 34. During a cryotherapy treatment process, the mass or plug 6 of $CO_2$ snow must be continually pressed up against the inner side 52 of the applicator cap to ensure that the plug has good thermal contact with the applicator cap 50. An appropriately sized spring or other suitable biasing means 70 is fitted around the push rod and travels along with the push rod and up into the applicator's interior. The distal end 72 of this spring presses against the back side of the base of the applicator while its proximal end 74 rest against a portion of an especially configured handle 80 that has a configuration adapted to allow the handle to be hand-operated to control the positioning of the applicator's tip 50 and either lock in position or incrementally advance the push rod and the plug of $CO_2$ snow.

Since, during a cryotherapy procedure, the plug 6 of $CO_2$ snow is slowly moving towards the distal end of the applicator, the interior wall 42 of the applicator near its distal end has been provided with a slight outward taper in order to aid the forward movement of this plug. For a normal preventive, ablation of cervical, precancerous lesions procedure, and consistent with the typical dimensions previously given for an applicator, a typical taper is in the range of 0.5-1.0 percent.

The handle 80 of the present invention is of a two-piece 82*a*, 82*b* construction and contains an opening 84 in the front face 86 of the handle and into which the proximal end 32 of the applicator is press fitted. This opening extends all the way through the handle and therefore allows the proximal end 62 of the push rod to extend from the rear face 88 of the handle. A spring-loaded trigger 90 is affixed to the handle and is configured such that a boundary edge 92 of the trigger interacts with grooves 60*a* on the push rod to provide the handle with its ability to incrementally advance or lock the push rod's position relative to the handle. The retraction of the push rod is handled manually (for example, to allow for the filling of the distal end of the applicator with $CO_2$ snow), i.e., the handle's trigger is pulled backward to release the push rod while the proximal end of the push rod is grasped in the free hand of the one who is holding the device's handle and pulled backward to retract the push rod.

Figure 3:
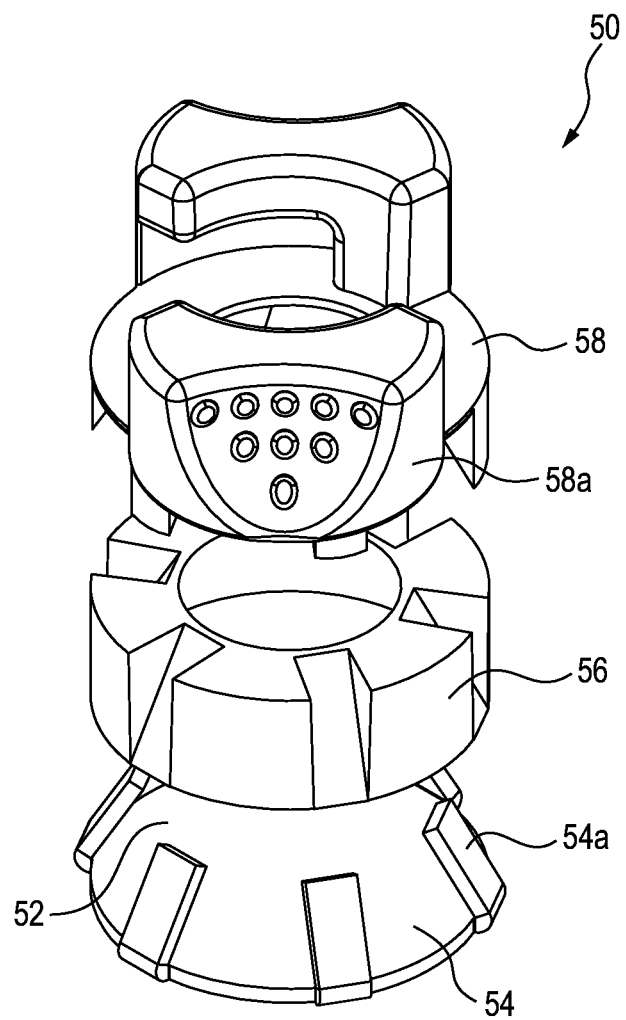
FIG. 3 is a perspective view of an applicator tip that is suitable for use in the present invention.

This device's applicator cap or tip 50 has a configuration adapted to allow it to be attached to and detached from the fitting 40 applicator's distal end and provide good thermal transfer through it since it is this tip that comes into contact with a patient and therefore needs an adequate rate of low-temperature thermal transfer from the mass of collected snow to the patient for the cryotherapy ablation process to be successful. This capability is provided by forming its outer surface 54 which comes into contact with a patient from metal while the remainder of the tip is normally formed from plastic. FIG. 3 shows an exploded perspective view of such an applicator tip where an intermediate ring 56 is used to help attaching the taps 54*a* of the metal outer surface to the ring 56 and it to the tip's connector 58 which has protrusions 58*a* on either side of it that aid in gripping the applicator tip. The intermediate ring 56 is then attached, usually via gluing, to the tip's connector 58.

The method or steps for using the present invention include:
1. Attaching the piping assembly to a siphoned $CO_2$ tank such that it's distal end points downward (note: if using a non-siphoned $CO_2$ tank, the distal end should point upward when the tank is valve side up),
2. Opening the outside packaging of the high level disinfected and/or sterilized components (i.e., snow horn, applicator, push rod, applicator cap, spring, handle) of the present invention without touching the interior of the wrapping.
3. Wiping down a small work surface on which to place the components that are to assembled to make the handle with a solution of 70% or 99% isopropyl alcohol
4. Wiping down the assembled handle and the on/off lever of the piping assembly with a solution of 70 or 90% isopropyl alcohol,
5. Putting on sterile or disinfected gloves,
6. Removing the snow horn and threading or attaching it to the distal end of the piping assembly until they are hand-tight, locked together,
7. Removing an applicator and inserting its proximal end into the opening in the handle's front face,
8. Dropping the spring into the applicator,
9. Placing the push rod into the applicator and spring with its proximal end going into and through the handle (squeeze the trigger to allow the push rod to pass all the way through), pulling back on the rod's proximal end once it is through the handle (rather than pushing from the rod's distal end) to completely retract the push rod and then releasing the trigger (don't release the push rod until trigger is completely locked into the grooves of the push rod),
10. Sliding the assembled handle and applicator into the snow horn, the tabs on the applicator's distal end go into the coupling on the snow horn's distal end (a click will indicate that it is fully seated),
11. On the piping assembly, turning the on/off valve to on; keeping it on until the $CO_2$ snow is visible above the fitting on the end of the snow horn—then, turning the valve to off,
12. Disconnecting the assembled handle and applicator from the snow horn by sliding it out the way it went in,
13. Sliding the applicator cap onto the distal end of the applicator and twisting it to lock it in place, the device is now ready to perform a freeze,
14. To freeze, simply squeeze the trigger, there will be a slight popping sound as the spring is released,
15. At the end of the freeze, release the trigger and it will lock the push rod in place; for a more rapid defrost, squeeze the trigger and retract the push rod to pull the $CO_2$ snow back away from the cap and release the trigger to lock the push rod, and
16. After the defrost, squeeze the trigger to unlock the push rod and pull the applicator out of the handle and drop the push rod, spring, applicator, and its cap into a decontaminating, chlorine solution.

For a cryotherapy process directed to the ablation of cervical, precancerous lesions to prevent cervical cancer, and utilizing what is called a "double freeze procedure," a second freeze would be completed by completing steps 7 through 16 after a five minute thaw cycle is completed and by using a second applicator set (i.e., push rod, spring, applicator and its cap) that would be provided with the device.

An alternative way to describe the method of the present invention is note that it is a method for providing a patient with cryotherapy ablation in which the steps for performing this method utilizing a connection to the outlet of a pressurized tank of a low-temperature liquid in association with the device as disclosed in the prior paragraphs.

Finally, it can be seen that the current invention eliminates many of the previously noted disadvantages (e.g., frequent tip blockages in the very expensive, gold or chrome plated nozzles that do not hold up well to frequently being disinfected; current devices on which these nozzles are used cost around thirteen hundred dollars per device; often considerable difficulty in maintaining such devices; need to transport with these devices fifty pound tanks of carbon dioxide tank; difficulty in scaling up the current process to accommodate large numbers of patients) in traditional cryotherapy processes.

The many features and advantages of the present invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to and are considered to fall within the scope of the present invention.

We claim:

1. A device that is adapted to connect to the outlet of a pressurized tank containing liquid carbon dioxide for providing a patient with cryotherapy process that is directed to the ablation of a lesion on said patient, said device comprising:
- a piping assembly having a distal and a proximal end and a configuration adapted to allow said distal end to connect to said pressurized tank outlet so as to create a spray of carbon dioxide snow as a result of the freezing of said carbon dioxide upon its exhaustion from said piping assembly,
- a tubular, snow horn having a distal and a proximal end, a boundary wall extending between said ends and enclosing the interior region of said snow horn, said snow horn also having a configuration adapted to allow said snow horn distal end to connect said piping assembly proximal end,
- a tubular applicator having a distal and a proximal end and a boundary wall extending between said ends and a configuration adapted to allow said applicator distal end to temporarily connect to said snow horn proximal end, and wherein said tubular applicator boundary wall having a plurality of vent holes,
- wherein said configurations of the tubular snow horn and the tubular applicator are further adapted to allow for the collection in said tubular applicator of a quantity of said carbon dioxide snow in the range of 8-10 grams and having a density in the range of 8-11 $g/in^3$,
- an applicator tip having an inner and outer surface that includes a metal portion and a configuration adapted to allow said applicator tip to connect to said applicator distal end during said cryotherapy process and to allow said metal portion of said outer surface of said applicator tip to come into contact with said patient, and
- a push rod having a distal end and a proximal end and a base attached to said push rod distal end and having a configuration adapted to allow said push rod distal end to variably extend into said tubular applicator from said applicator proximal end so as to allow said push rod base to serve as the furthest point in said tubular applicator from said applicator distal end that said spray of carbon dioxide snow can collect.

2. The device as recited in claim 1, further comprising:
a handle having a configuration adapted to allow said handle to be hand-operated to control the positioning of said distal end of said tubular applicator during said cryotherapy process.

3. The device as recited in claim 1, further comprising:
a means for biasing said push rod so as to cause said push rod base to push said mass of collected carbon dioxide snow towards and against said applicator tip during said cryotherapy process.

4. The device as recited in claim 2, further comprising:
a means for biasing said push rod so as to cause said push rod base to push said mass of collected carbon dioxide snow towards and against said applicator tip during said cryotherapy process.

5. The device as recited in claim 2, wherein:
said push rod configuration further adapted to interact with said handle to control the location of said base relative to said tubular applicator distal end.

6. The device as recited in claim 3, wherein:
said push rod configuration further adapted to interact with said handle to control the location of said base relative to said tubular applicator distal end.

7. The device as recited in claim 1, wherein:
said piping assembly, tubular snow horn, tubular applicator and applicator tip configurations are all further adapted for when said patient is a human.

8. The device as recited in claim 1, wherein:
said piping assembly, tubular snow horn, tubular applicator and applicator tip configurations are all further adapted for a cryotherapy process that is directed to the removal of cervical, precancerous lesions for the prevention of cervical cancer.

* * * * *